United States Patent [19]

Hoffmann et al.

[11] 4,139,615
[45] Feb. 13, 1979

[54] O-ALKYL-S-ALKYL-O-(4-TRI-FLUOROMETHYLTHIO-PHENYL)-(THIONO)-THIOL-PHOSPHORIC ACID ESTERS AND PESTICIDAL COMPOSITIONS AND METHODS

[75] Inventors: Hellmut Hoffmann, Wuppertal; Erich Klauke; Ingeborg Hammann, both of Colonge; Wilhelm Stendel, Wuppertal, all of Fed. Rep. of Germany

[73] Assignee: Bayer Aktiengesellschaft, Leverkusen, Fed. Rep. of Germany

[21] Appl. No.: 798,746

[22] Filed: May 19, 1977

[30] Foreign Application Priority Data

Jun. 9, 1976 [DE] Fed. Rep. of Germany ....... 2625764

[51] Int. Cl.² .......................... A01N 9/36; C07F 9/165
[52] U.S. Cl. ...................................... 424/216; 260/949
[58] Field of Search ......................... 260/949; 424/216

[56] References Cited
U.S. PATENT DOCUMENTS

| | | | |
|---|---|---|---|
| 3,162,672 | 12/1964 | Richert et al. | 260/949 |
| 3,825,636 | 7/1974 | Kishino et al. | 260/949 X |
| 3,839,511 | 10/1974 | Kishino et al. | 260/949 X |
| 3,904,710 | 9/1975 | Oswald et al. | 260/949 |
| 3,969,444 | 7/1976 | Oswald et al. | 260/949 X |
| 4,013,794 | 3/1977 | Maurer et al. | 260/949 X |
| 4,067,972 | 1/1978 | Oswald et al. | 260/949 X |

*Primary Examiner*—Anton H. Sutto
*Attorney, Agent, or Firm*—Sprung, Felfe, Horn, Lynch & Kramer

[57] ABSTRACT

O-Alkyl-S-alkyl-O-(4-trifluoromethylthiophenyl)-(thiono)-thiol-phosphoric acid esters of the formula

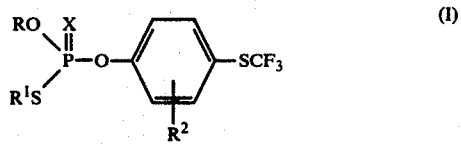

in which
R and $R^1$ each independently is alkyl,
$R^2$ is hydrogen or alkyl, and
X is oxygen or sulphur, which possess insecticidal, acaricidal and nematicidal properties.

8 Claims, No Drawings

O-ALKYL-S-ALKYL-O-(4-TRIFLUOROMETH- YLTHIO-PHENYL)-(THIONO)-THIOL-PHOS- PHORIC ACID ESTERS AND PESTICIDAL COMPOSITIONS AND METHODS

The present invention relates to and has for its objects the provision of particular new O-alkyl-S-alkyl-O-(trifluoromethylthio-phenyl)-(thiono)-thiol-phosphoric acid esters which possess insecticidal, acricidal and nematicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DAS 1,153,747 that trifluoromethylthio-phenyl-thionophosphoric (phosphonic) acid esters, for example O,O-dimethyl-O(3-methyl-4-trifluoromethylthio-phenyl)-thiono-phosphoric acid ester (Compound A) and O-ethyl-O-(2-methyl-4-trifluoromethylthio-phenyl)-thiono-ethanephosphonic acid ester (Compound B), possess insecticidal and acaricidal properties.

The present invention provides new trifluoromethylthiophenyl-(di)-thio-phosphoric acid esters of the formula $$\underset{R^1S}{\overset{RO}{>}}\overset{X}{\underset{\|}{P}}-O-\phenyl(R^2)-SCF_3 \quad (I)$$

in which
R and $R^1$ each independently is alkyl,
$R^2$ is hydrogen or alkyl, and
X is oxygen or sulphur.

Preferably, R is straight-chain or branched alkyl with 1 to 3 carbon atoms, $R^1$ is straight-chain or branched alkyl with 1 to 4 carbon atoms, and $R^2$ is hydrogen or methyl.

R is most preferably ethyl, $R^1$ is most preferably n-propyl, and $R^2$ is most preferably methyl.

Surprisingly, the trifluoromethylthio-phenyl (di)thiophosphoric acid esters according to the invention possess a better insecticidal, acaricidal and nematicidal action than the compounds of analogous structure, and of the same type of action, previously known from the literature. The compounds according to the present invention thus represent a genuine enrichment of the art.

The invention also provides a process for the preparation of a trifluoromethylthio-phenyl-(di)-thio-phosphoric acid ester (I) in which (a) an O,S-dialkyl(di-)-thiophosphoric acid diester halide of the formula $$\underset{R^1S}{\overset{RO}{>}}\overset{X}{\underset{\|}{P}}-Hal \quad (II)$$

in which
R, $R^1$ and X have the abovementioned meanings and Hal is halogen, preferably chlorine,
is reacted with a 4-trifluoromethylthio-phenol of the formula $$HO-\phenyl(R^2)-SCF_3 \quad (III)$$

in which
$R^2$ has the abovementioned meaning,
optionally in the presence of an acid acceptor and optionally in the presence of a solvent or diluent, or (b) an O,O-dialkyl-O-(4-trifluoromethylthio-phenyl)-thionophosphoric acid ester of the formula $$(Alkyl-O)_2\overset{S}{\underset{\|}{P}}-O-\phenyl(R^2)-SCF_3 \quad (IV)$$

in which
$R^2$ has the abovementioned meaning and
Alkyl is $C_{1-6}$ alkyl,
is reacted first with an alkali metal xanthate of the formula $$MS-\overset{S}{\underset{\|}{C}}-OAlkyl \quad (V)$$

in which
Alkyl has the abovementioned meaning and
M is an alkali metal, preferably sodium or potassium,
and subsequently with an alkyl halide of the formula $$R^1-Hal^1 \quad (VI)$$

in which
$R^1$ has the abovementioned meaning and
$Hal^1$ is halogen, preferably chlorine or bromine,
optionally in the presence of a solvent or diluent.

If, for example, O-ethyl-S-n-butylthionothiolphosphoric acid diester chloride and 4-trifluoromethylthiophenol, or O,O-diethyl-O-(4-trifluoromethylthiophenyl)-thionophosphoric acid ester, potassium ethylxanthate and 1-bromo-n-butane are used as starting materials, the course of the reaction of the two process variants (a) and (b) can be represented by the following formula schemes:

$$\underset{n-C_4H_9S}{\overset{C_2H_5O}{>}}\overset{S}{\underset{\|}{P}}-Cl + HO-\phenyl-SCF_3 \quad (a)$$

$$\xrightarrow{\text{Acid acceptor}}_{-HCl} \underset{n-C_4H_9S}{\overset{C_2H_5O}{>}}\overset{S}{\underset{\|}{P}}-O-\phenyl-SCF_3$$

$$(C_2H_5O)_2\overset{S}{\underset{\|}{P}}-O-\phenyl-SCF_3 + \quad (b)$$

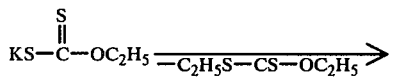

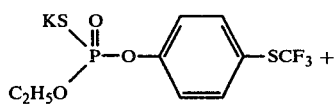

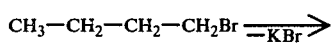

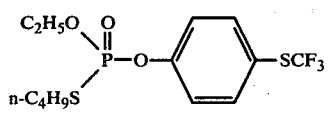

The O,S-di-alkyl(di)-thiophosphoric acid diester halides (II) are known and can be prepared according to customary processes, as can the 4-trifluoromethylthiophenols (III), the O,O-dialkyl-O-(4-trifluoromethylthiophenyl)-thiono-phosphoric acid esters (IV), the alkali metal xanthates (V) and the alkyl halides (VI).

The following may be mentioned as examples of the O,S-dialkyl(di)-thiophosphoric acid diester halides (II): O,S-dimethyl-, O,S-diethyl-, O,S-di-n-propyl-, O,S-di-isopropyl-, O,S-di-n-butyl-, O,S-di-iso-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethylthiolphosphoric acid diester chloride and the corresponding thiono analogues.

The following may be mentioned as examples of the 4-trifluoromethylthio-phenols (III): 4-trifluoromethyl-thiophenol and 3-methyl-4-trifluoromethylthio-phenol.

The following may be mentioned as examples of the O,O-dialkyl-O-(4-trifluoromethylthio-phenyl)-thionophosphoric acid esters (IV): O,O-dimethyl-O-(4-trifluoromethylthio-phenyl)-thionophosphoric acid ester, O,O-diethyl-O-(4-trifluoromethylthio-phenyl)-thionophosphoric acid ester, O,O-di-n-propyl-O-(4-trifluoromethylthio-phenyl)-thionophosphoric acid ester, O,O-dimethyl-O-(3-methyl-4-trifluoromethylthio-phenyl)-thionophosphoric acid ester, O,O-diethyl-O-(3-methyl-4-trifluoromethylthio-phenyl)-thionophosphoric acid ester and O,O-di-n-propyl-O-(3-methyl-4-trifluoromethylthio-phenyl)-thionophosphoric acid ester.

Sodium xanthate and potassium xanthate may be mentioned as examples of xanthates (V).

The following may be mentioned as examples of the alkyl halides (VI): bromomethane, bromoethane, 1-bromopropane, 2-bromopropane and 1-bromobutane.

The reaction of the process for the preparation of the compounds according to the invention is preferably carried out in the presence of a solvent or diluent. Virtually all inert organic solvents can be used for this purpose. These include, in particular, aliphatic and aromatic, optionally chlorinated, hydrocarbons, for example benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, for example acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly successful, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at 0 to 120° C., preferably at 20 to 85° C.

In general, the reaction is allowed to take place under normal pressure.

To carry out process variant (a), the starting materials are preferably employed in equimolar ratio. An excess of one or other component produces no essential advantages. The reactants are in general brought together in one of the stated solvents, in the presence of an acid acceptor, and are stirred for one or more hours, in most cases at an elevated temperature, to complete the reaction.

Thereafter an organic solvent, for example toluene, may be added to the mixture, and the organic phase may be worked up in the usual manner by washing, drying and distilling off the solvent.

To carry out process variant (b), the xanthate is preferably added in 10–15% excess to the phosphoric acid ester, and the reaction mixture is boiled for several hours under reflux, cooled and mixed with water and ether. The phases are separated, the aqueous phase is filtered, the water is distilled off and the oil which is mixed, without further purification, with an excess of alkyl halide, if appropriate in the presence of a solvent, and heated for several hours under reflux. After the mixture has cooled, an organic solvent, for example toluene, is added thereto, and the organic phase is worked up in the usual manner by washing, drying and distilling off the solvent.

The new compounds are obtained in the form of water-insoluble oils, which in some cases cannot be distilled without decomposition, but can be freed from the last volatile constituents by so-called "slight distillation", that is to say by prolonged heating under reduced pressure to moderately elevated temperatures, and they can be purified in this manner. They are characterized by the refractive index.

As already mentioned, the trifluoromethylthio-phenyl(di)-thio-phosphoric acid esters according to the invention are distinguished by an excellent insecticidal, acaricidal and nematicidal activity. They are not only active against plant pests, hygiene pests and pests of stored products, but also, in the veterinary medicine field, against animal parasites (ectoparasites), such as parasitic fly larvae, and combine a low phytotoxicity with a good action against both sucking and biting insects and mites.

For this reason, the compounds according to the invention can be employed successfully as pesticides in plant protection as well as in the hygiene field, the field of protection of stored products and the veterinary field.

The active compounds are well tolerated by plants, have a favorable level of toxicity to warm-blooded animals, and can be used for combating animal pests, especially insects, arachnida and nematodes which are encountered in agriculture, in forestry, in the protection of stored products and of materials, and in the hygiene field. They are active against normally sensitive and resistant species and against all or some stages of development. The abovementioned pests include:

From the order of the *Isopoda*, for example *Oniscus asellus, Armadillidium vulgare* and *Porcellio scaber.* From the order of the *Diplopoda*, for example *Blaniulus guttulatus.* From the order of the *Chilopoda*, for example *Geophilus carpophagus* and *Scutigera* spec. From the order of the *Symphyla*, for example *Scutigerella immaculata.* From the order of the *Thysanura*, for example *Lepisma saccharina.* From the order of the *Collembola*, for example *Onychiurus armatus.* From the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example *Forficula auricularia.* From the order of the Isoptera, for example Reticulitermes spp. From the order of the Anoplura, for example *Phylloxera vastatrix,* Pemphigus spp., *Pediculus humanus corporis,* Haematopinus spp. and Linognathus spp. From the order of the Mallophaga, for example Trichodectes spp, and Damalinea spp. From the order of the Thysanoptera, for example, *Hercinothrips femoralis* and *Thrips tabaci.* From the order of the Heteroptera, for example Eurygaster spp., *Dysdercus intermedius, Piesma quadrata, Cimex lectularius, Rhodnius prolixus* and Triatoma spp. From the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium cornl, Saissetia oleae, Laodelphax striatellus, Nilaparvata lugens, Aonidiella aurantii, Aspidiotus hederae,* Pseudococcus spp. and Psylla spp.. From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana.* From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., Meligethes aeneus, Ptinus spp., *Niptus hololeucus, Gibbium psylloides,* Tribolium spp., *Tenebrio molitor,* Agriotes spp., Conoderus spp., *Melolontha melolontha, Amphimallon Solstitalis* and *Costelytra zealandica.* From the order of the Hymenoptera, for example Diprion spp., Hoplocampa spp., Lasius spp., *Monomorium pharaonis* and Vespa spp. From the order of the Diptera, for example Aëdes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio Hortulanus, Oscinella frit,* Phorbia spp., *Pegomyia Hyoscyami, Ceratitis capitata, Dacus oleae* and *Tipula paludosa.* From the order of the Siphonaptera, for example *Xenopsylla cheopis* and Ceratophyllus spp.. From the order of the Arachnida, for example *Scorpio maurus* and *Latrodectus mactans.* From the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp., The plant-parasitic nematodes include Pratylenchus spp., *Radopholus similis, Ditylenchus dipsaci, Tylenchulus semipenetrans,* Heterodera spp., Meloidogyne spp, Aphelenchoides spp., Longidorus spp., Xiphinema spp. and Trichodorus spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, dichlorodifluoromethane, trichlorofluoromethane, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid alumina and silicates; as solid carriers for granules; crushed and fractionated natural rocks such as calcite, marble, pumice sepiolite and dolomite, as well as synthetic granules of inorgan and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigements, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other insecticides, and acaricides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100%, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, (c) such nematodes and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidal effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, funigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Myzus Test (Contact Action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from Table 1:

Table 1
(Myzus Test)

| Active compound | Active compound concentration in % by weight | Degree of destruction in % after 1 day |
|---|---|---|
| $C_2H_5O\text{-}P(=S)(C_2H_5)\text{-}O\text{-}C_6H_3(CH_3)\text{-}S\text{-}CF_3$ (known) (B) | 0.1<br>0.01 | 100<br>0 |
| $F_3CS\text{-}C_6H_4\text{-}O\text{-}P(=S)(OC_2H_5)(SC_3H_7\text{-}n)$ (1) | 0.1<br>0.01 | 100<br>100 |
| $F_3CS\text{-}C_6H_3(CH_3)\text{-}O\text{-}P(=S)(OC_2H_5)(SC_3H_7\text{-}n)$ (2) | 0.1<br>0.01 | 100<br>98 |
| $F_3CS\text{-}C_6H_3(CH_3)\text{-}O\text{-}P(=O)(OC_2H_5)(SC_3H_7\text{-}n)$ (3) | 0.1<br>0.01 | 100<br>100 |

EXAMPLE 2

Tetranychus Test (Resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the common or two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from Table 2;

Table 2
(Tetranychus Test)

| Active compound | Active compound concentration in % by weight | Degree of destruction in % after 2 days |
|---|---|---|
| $(CH_3O)_2P(=S)\text{-}O\text{-}C_6H_3(CH_3)\text{-}SCH_3$ (known) (A) | 0.1 | 0 |
| $F_3CS\text{-}C_6H_3(CH_3)\text{-}O\text{-}P(=S)(OC_2H_5)(SC_3H_7\text{-}n)$ (2) | 0.1 | 100 |
| $F_3CS\text{-}C_6H_3(CH_3)\text{-}O\text{-}P(=O)(OC_2H_5)(SC_3H_7\text{-}n)$ (3) | 0.1 | 100 |

EXAMPLE 3

Test with Parasitic Fly Larvae

Solvent:
 35 parts by weight of ethylene polyglycol monomethyl ether
 35 parts by weight of nonylphenol polyglycol ether To produce a suitable preparation of active compound, 30 parts by weight of the active substance in question were mixed with the stated amount of solvent which contained the abovementioned proportion of emulsifier and the concentrate thus obtained was diluted with water to the desired concentration.

About 20 fly larvae (*Lucilia cuprina*) were introduced into a test tube which contained approx. 2 cm³ of horse muscle. 0.5 ml of the preparation of active compound was applied to this horse meat. After 24 hours, the degree of destruction in % was determined. 100% means that all larvae had been killed and 0% means that no larvae had been killed.

The active compounds tested, active compound concentrations used and results obtained can be seen from Table 3.

Table 3
(Test with parasitic fly larvae (*Lucilia cuprina*))

| Active compound | Active compound concentration in ppm | Degree of destruction in % |
|---|---|---|
| $C_2H_5O\text{-}P(=S)(S\text{-}n\text{-}C_3H_7)\text{-}O\text{-}C_6H_4\text{-}SCF_3$ (1) | 100<br>30<br>10 | 100<br>100<br>100 |
| $C_2H_5O\text{-}P(=O)(S\text{-}n\text{-}C_3H_7)\text{-}O\text{-}C_6H_3(CH_3)\text{-}SCF_3$ (3) | 100<br>30<br>10 | 100<br>100<br>100 |

EXAMPLE 4

Test Nematode: *Meloidogyne incognita*

Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness is 100% when infestation was completely avoided; it is 0% when the infestation was exactly the same as in the case of the control plants in untreated soil which had been infested in the same manner.

The active compounds, the amounts applied and the results can be seen from the following Table 4:

Table 4

| Active compound | (*Meloidogyne incognita*) Degree of destruction in % at an active compound concentration of 5 ppm |
|---|---|
| CH₃O\\P(=S)/OCH₃ —O—C₆H₃(CH₃)—S—CF₃ (known) (A) | 0 |
| F₃CS—C₆H₄—O—P(=S)(OC₂H₅)(S—C₃H₇-n) (1) | 100 |

The following further examples are set forth to illustrate, without limitation, the manner of producing the instant compounds according to the present invention:

EXAMPLE 5

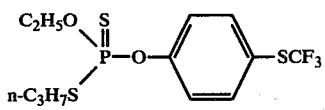

(1)

19.4 g (0.1 mol) of 4-trifluoromethylthio-phenol were dissolved in 100 cm³ of acetonitrile in a stirred flask equipped with a dropping funnel and thermometer, and 15 g (10% excess) of potassium carbonate powder were added to the resulting solution. 22 g (0.1 mol) of O-ethyl-S-n-propyl-dithiophosphoric acid diester chloride were added dropwise over the course of 20 minutes to this suspension. In the course thereof, the temperature rose from 25 to 48° C. The batch was stirred for a further 2 hours at room temperature and was taken up in toluene, and the toluene solution was washed successively with water, 5% strength sodium hydroxide solution and again with water. The organic phase was dried over sodium sulphate, filtered and freed from the solvent under reduced pressure. 34.2 g (91% of theory) of O-ethyl-S-n-propyl-O-(4-trifluoromethylthio-phenyl)-thionothiol-phosphoric acid ester were obtained in the form of a light yellow water-insoluble oil of refractive index $n_D^{25}$: 1.5282.

The compound of the formula

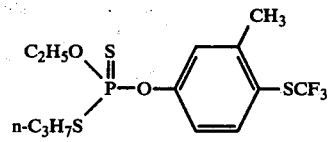

(2)

was prepared analogously. The yield was 82% of theory. The product had a refractive index $n_D^{22}$: 1.5283.

EXAMPLE 6

(a)

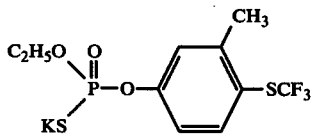

(Va)

45 g (0.28 mol) of potassium xanthate were added to a solution of 90 g (0.25 mol) of O,O-diethyl-O-(3-methyl-4-trifluoromethylthio-phenyl-)thionophosphoric acid ester in 250 cm³ of acetonitrile, the mixture was then boiled for about 4 hours under reflux, the reaction mixture was cooled to room temperature and 200 cm³ of water and 200 cm³ of diethyl ether were added. The lower, aqueous phase was carefully separated off in a separating funnel and freed from adhering solvent residues by filtration through a filter paper. After distilling off the water under reduced pressure, 93 g (about 100% of theory) of potassium O-ethyl-O-(3-methyl-4-trifluoromethylthio-phenyl)-thiolphosphate remained in the form of a viscous oil, which could be reacted further without additional purification.

(b)

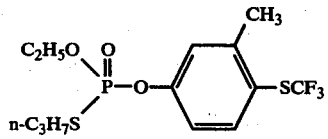

(3)

40 g (0.32 mol) of 1-bromopropane were added to a solution of 93 g (0.25 mol) of potassium-O-ethyl-O-(3-methyl-4-trifluoromethylthiophenyl)-thiolphosphate, obtainable as described under (a), in 200 cm³ of acetonitrile, and the mixture was boiled for 3 hours under reflux. After the solution had cooled, it was diluted with toluene and twice washed with water, and after separating off the organic phase, the latter was dried over sodium sulphate and filtered, and the solvent was distilled from the filtrate under reduced pressure.

69 g (74% of theory) of O-ethyl-S-n-propyl-O-(3-methyl-4-trifluoromethylthio-phenyl)-thiolphosphoric acid ester were obtained as a light yellow water-insoluble oil of refractive index $n_D^{25}$: 1.5009.

It will be appreciated that the instant specification and examples are set forth by way of illustration and not limitation, and that various modifications and changes may be made without departing from the spirit and scope of the present invention.

What is claimed is:

1. An O-alkyl-S-alkyl-O-(4-trifluoromethylthiophenyl)-thiolphosphoric acid ester of the formula

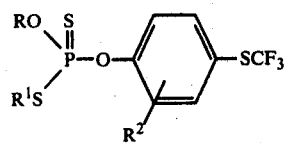

in which
R and $R^1$ each independently is alkyl, and
$R^2$ is hydrogen or 3 methyl.

2. A method of combating insect, acarid or nematode, pests which comprises applying to the pestes or a habitat thereof of an insecticidally, acaricidally or nematicidally effective amount of a compound according to claim 1.

3. A compound according to claim 1, in which
R is alkyl with 1 to 3 carbon atoms, and
$R^1$ is alkyl with 1 to 4 carbon atoms.

4. A compound according to claim 3, in which
R is ethyl, and
$R^1$ is n-propyl.

5. A compound according to claim 1, in which said compound is O-ethyl-S-n-propyl-O-(4-trifluoromethylthio-phenyl)-thionothiolphosphoric acid ester of the formula

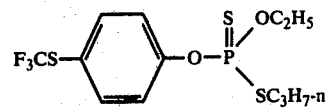

6. A compound according to claim 1, in which said compound is O-ethyl-S-n-propyl-O-(3-methyl-4-trifluoromethylthiophenyl)-thionothiol-phosphoric acid ester of the formula

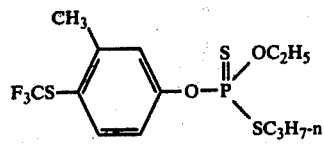

7. An insecticidal, acaricidal or nematicidal composition containing as active ingredient an insecticidally, acaricidally or nematicidally effective amount of a compound according to claim 1 in admixture with a diluent.

8. The method according to claim 2 in which said compound is O-ethyl-S-n-propyl-O-(4-trifluoromethylthio-phenyl)-thionothiolphosphoric acid ester, or
O-ethyl-S-n-propyl-O-(3-methyl-4-trifluoromethylthio-phenyl)-thionothiolphosphoric acid ester.